US008262564B2

(12) United States Patent
Masaki

(10) Patent No.: US 8,262,564 B2

(45) Date of Patent: Sep. 11, 2012

(54) POWER TRANSMISSION APPARATUS FOR ELECTRIC BENDING ENDOSCOPE

(75) Inventor: Yutaka Masaki, Mitaka (JP)

(73) Assignee: Olympus Medical Systems Corp. (JP)

( * ) Notice: Subject to any disclaimer, the term of this patent is extended or adjusted under 35 U.S.C. 154(b) by 1039 days.

(21) Appl. No.: 12/129,822

(22) Filed: May 30, 2008

(65) Prior Publication Data

US 2008/0312503 A1 Dec. 18, 2008

(30) Foreign Application Priority Data

Jun. 18, 2007 (JP) ................................ 2007-160502

(51) Int. Cl.
*A61B 1/00* (2006.01)

(52) U.S. Cl. ....... 600/146; 600/152; 192/3.62; 192/3.63

(58) Field of Classification Search .................. 600/146, 600/152; 192/3.62, 3.63
See application file for complete search history.

(56) References Cited

U.S. PATENT DOCUMENTS

| | | | | |
|---|---|---|---|---|
| 7,060,027 | B2 * | 6/2006 | Maeda et al. | 600/150 |
| 7,938,773 | B2 * | 5/2011 | Kawai et al. | 600/152 |
| 2004/0073083 | A1 | 4/2004 | Ikeda et al. | |
| 2004/0073085 | A1 * | 4/2004 | Ikeda et al. | 600/101 |
| 2004/0193014 | A1 * | 9/2004 | Miyagi et al. | 600/146 |
| 2004/0193015 | A1 * | 9/2004 | Ikeda et al. | 600/146 |
| 2004/0267093 | A1 * | 12/2004 | Miyagi et al. | 600/146 |
| 2006/0100484 | A1 * | 5/2006 | Maeda et al. | 600/146 |
| 2006/0261770 | A1 * | 11/2006 | Kishi et al. | 318/568.11 |
| 2007/0112255 | A1 * | 5/2007 | Ikeda et al. | 600/146 |
| 2007/0232856 | A1 * | 10/2007 | Ueno et al. | 600/118 |
| 2007/0265500 | A1 * | 11/2007 | Koitabashi et al. | 600/146 |
| 2008/0249365 | A1 * | 10/2008 | Masaki | 600/152 |
| 2008/0262306 | A1 * | 10/2008 | Kawai | 600/118 |

FOREIGN PATENT DOCUMENTS

| | | |
|---|---|---|
| EP | 1 738 678 A1 | 1/2007 |
| EP | 1 839 552 A1 | 10/2007 |
| JP | 2-164332 | 6/1990 |
| JP | 5-95896 | 4/1993 |
| JP | 6-285011 | 10/1994 |

(Continued)

OTHER PUBLICATIONS

Letter from German Associate to Japanese Associate enclosing European Search Report with Japanese Associate's receipt of service stamp dated Aug. 2, 2010.

(Continued)

*Primary Examiner* — John P Leubecker
*Assistant Examiner* — Arnaldo Torres Diaz
(74) *Attorney, Agent, or Firm* — Ostrolenk Faber LLP

(57) ABSTRACT

A power transmission apparatus for an electric bending endoscope includes an actuating member switchable between a connection position to bring a clutch mechanism into a connection state and a release position to bring the clutch mechanism into a release state, the actuating member being interlocked with the clutch mechanism, an electric drive mechanism being interlocked with the actuating member, and a manual drive mechanism including an operation member manually switchable to at least one of a connection drive position to bring the actuating member into the connection position and a release drive position to bring the actuating member into the release position, and a selective actuation transmission mechanism provided between the operation member and the actuating member and to transmit the actuation of the operation member to the actuating member and absorb the actuation of the actuating member without transmitting the actuation to the operation member.

14 Claims, 11 Drawing Sheets

FOREIGN PATENT DOCUMENTS

| | | |
|---|---|---|
| JP | 2001-95754 | 4/2001 |
| JP | 2003-275168 | 9/2003 |
| JP | 2004-174224 | 6/2004 |
| JP | 2006-192201 | 7/2006 |
| WO | WO 2006/059722 A1 | 6/2006 |

OTHER PUBLICATIONS

Search Report issued by European Patent Office in connection with corresponding application No. EP 08 010 038.1 on Jul. 14, 2010.

Japanese Office Action issued in corresponding Japanese Application No. 2007-160502 mailed on Mar. 6, 2012 with English translation.

* cited by examiner

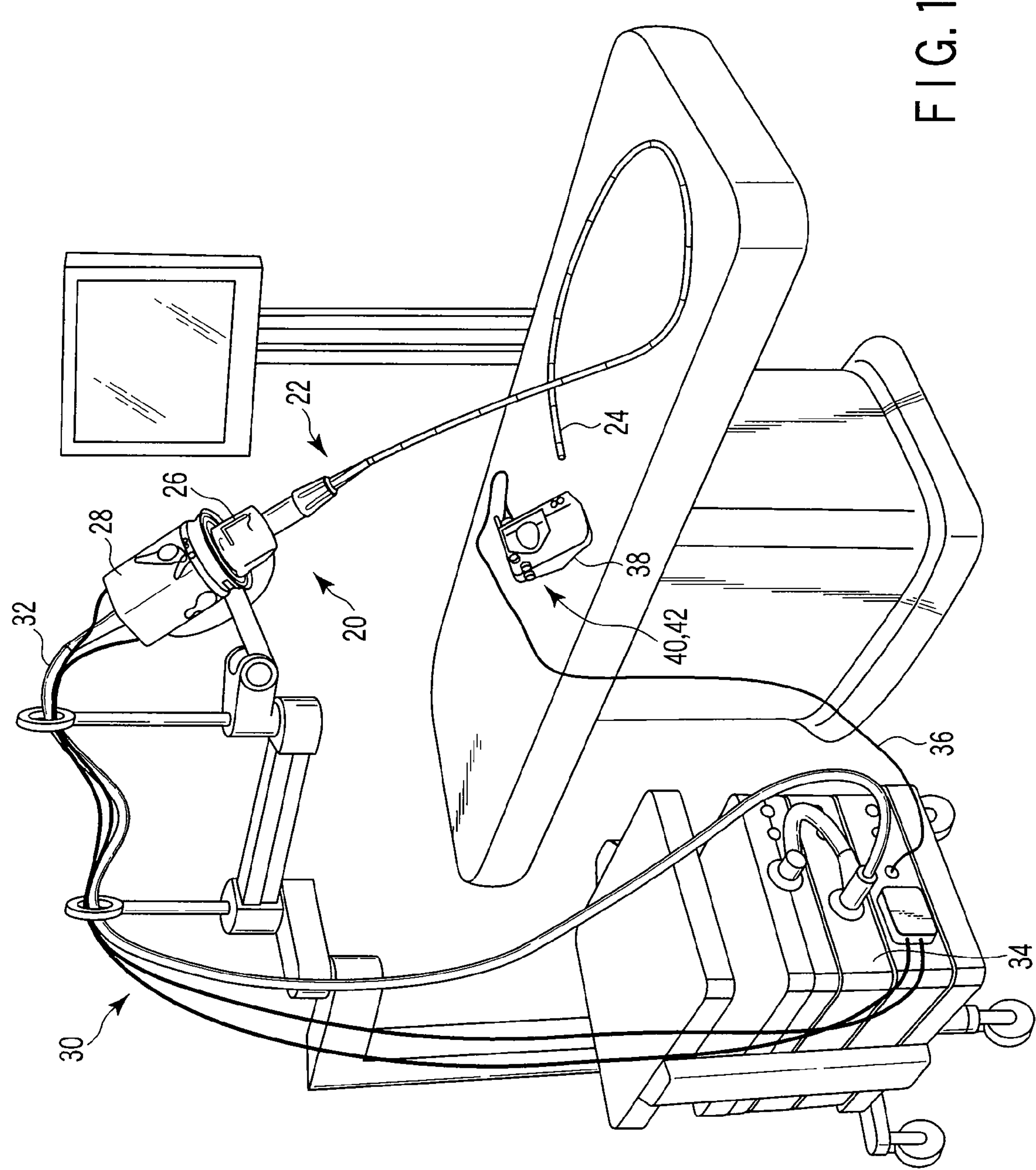
F I G. 1

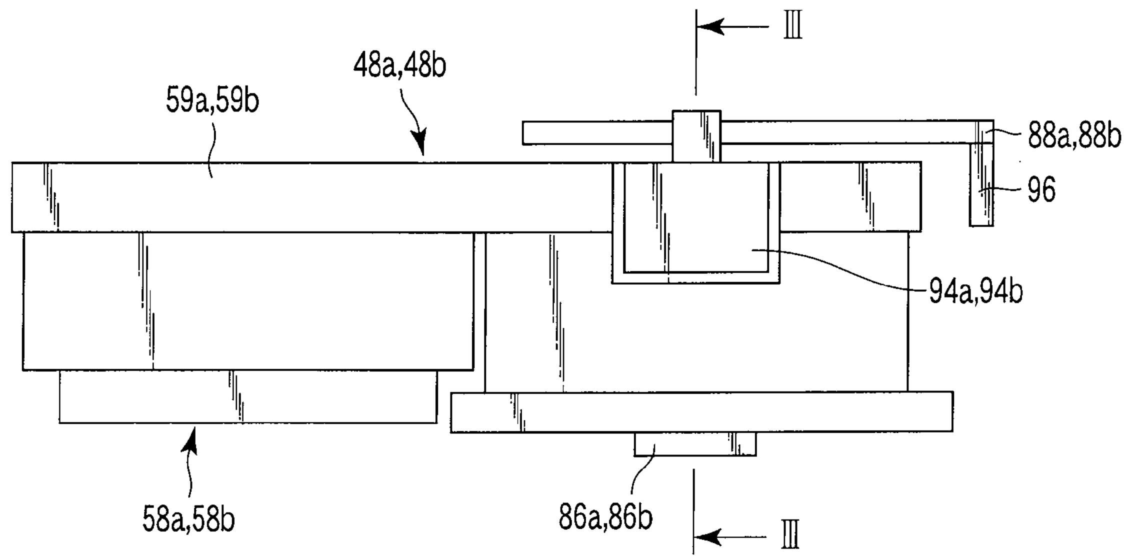
F I G. 2
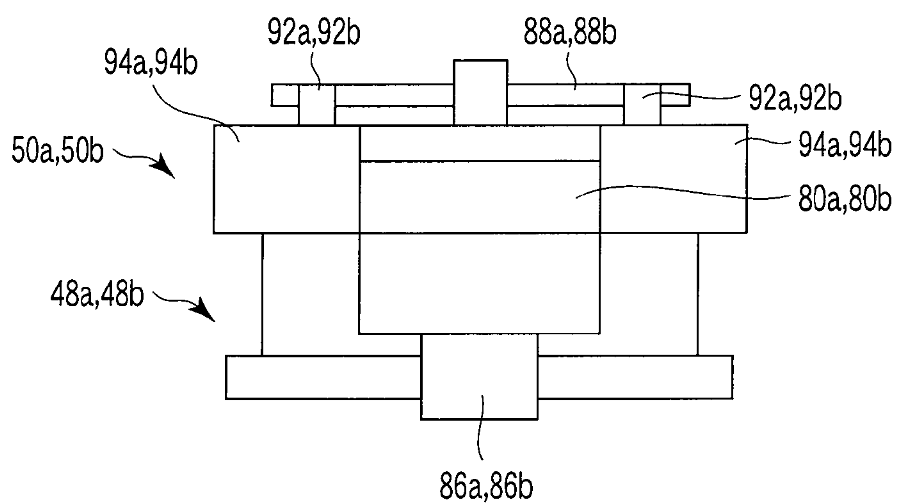
F I G. 3

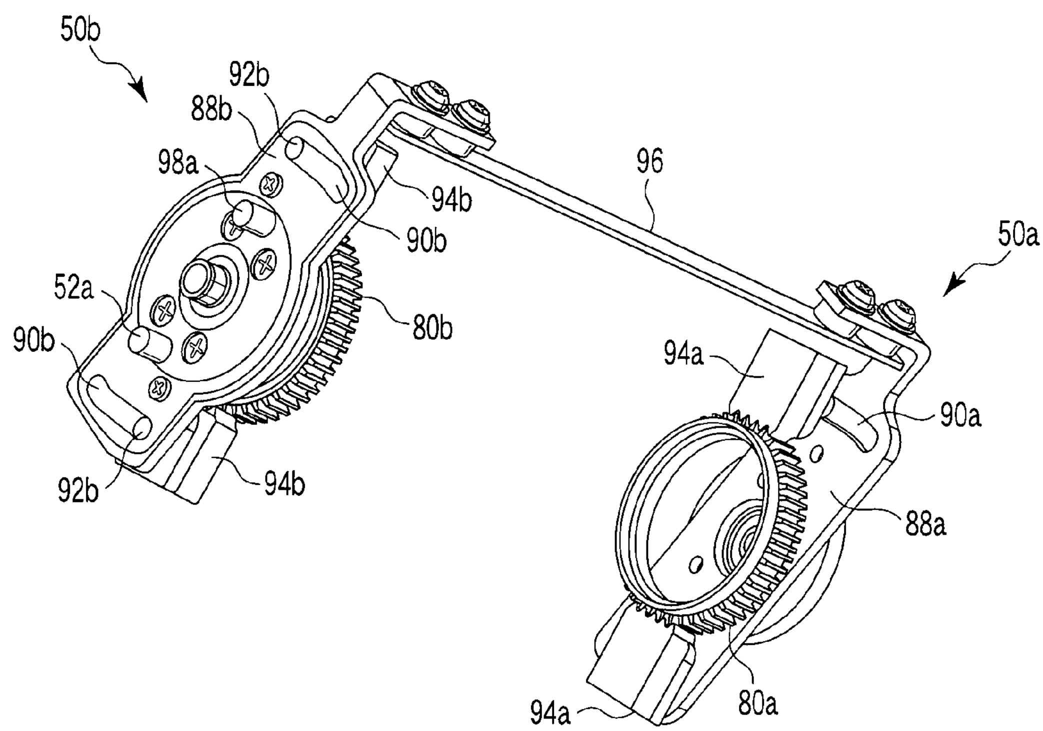
F I G. 5
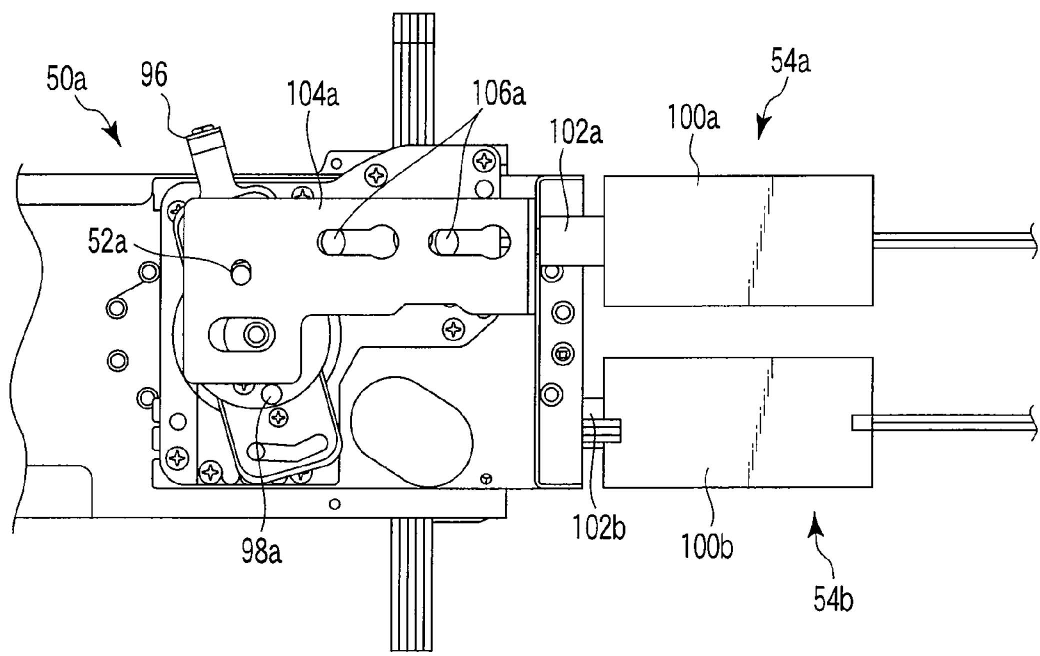
F I G. 6

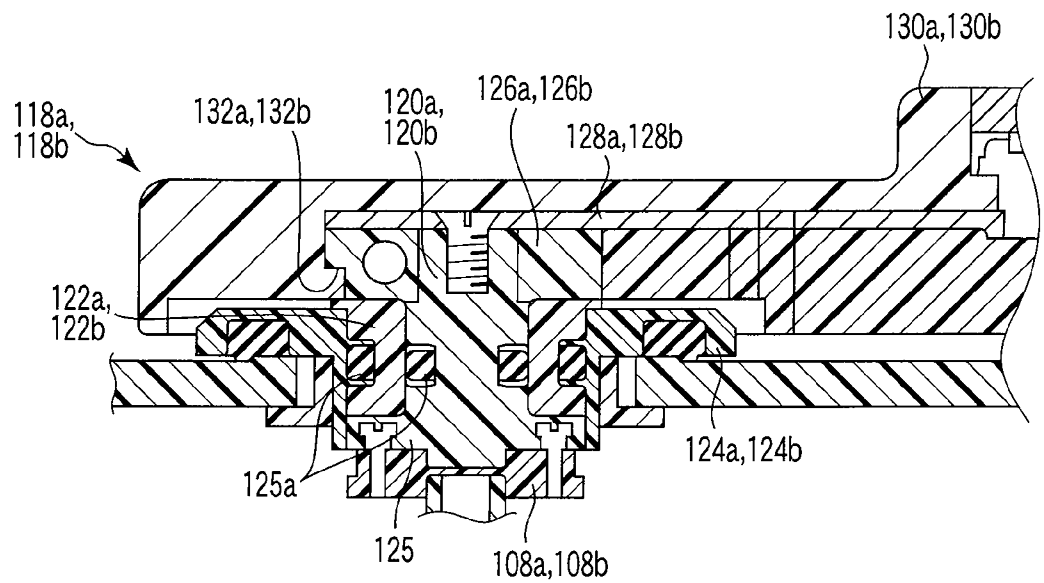
F I G. 10
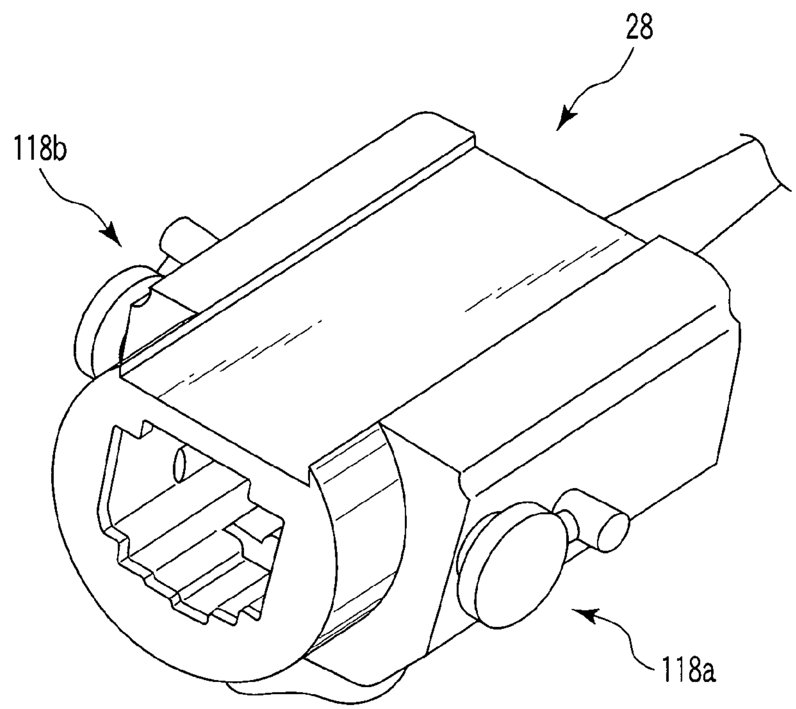
F I G. 11

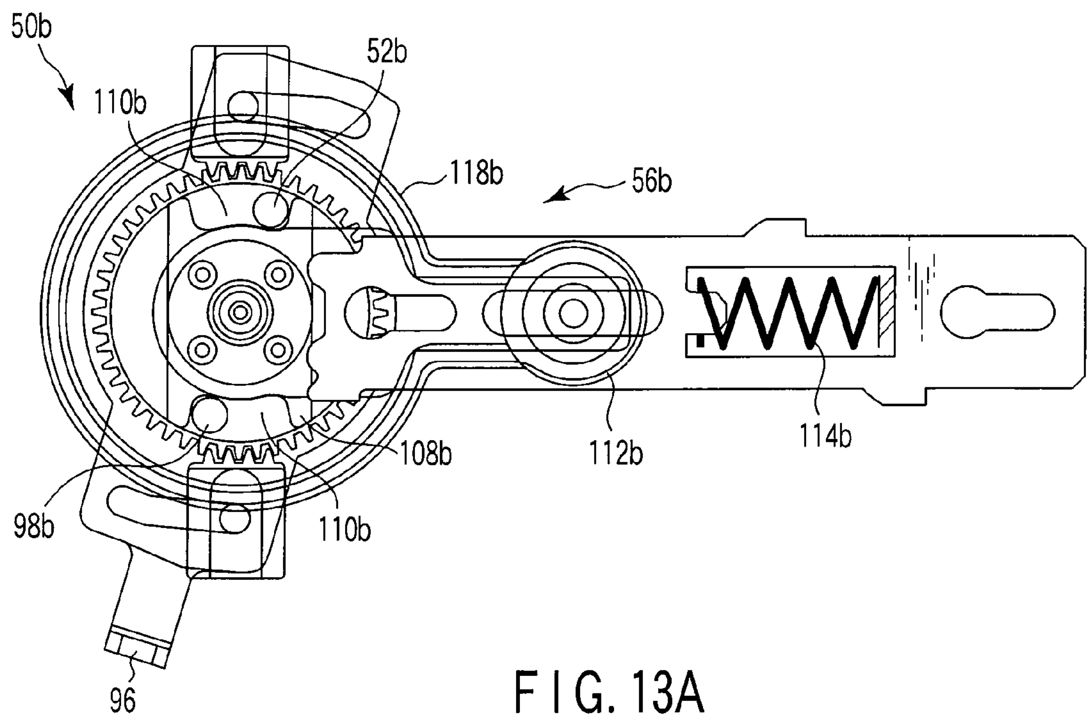
F I G. 13A
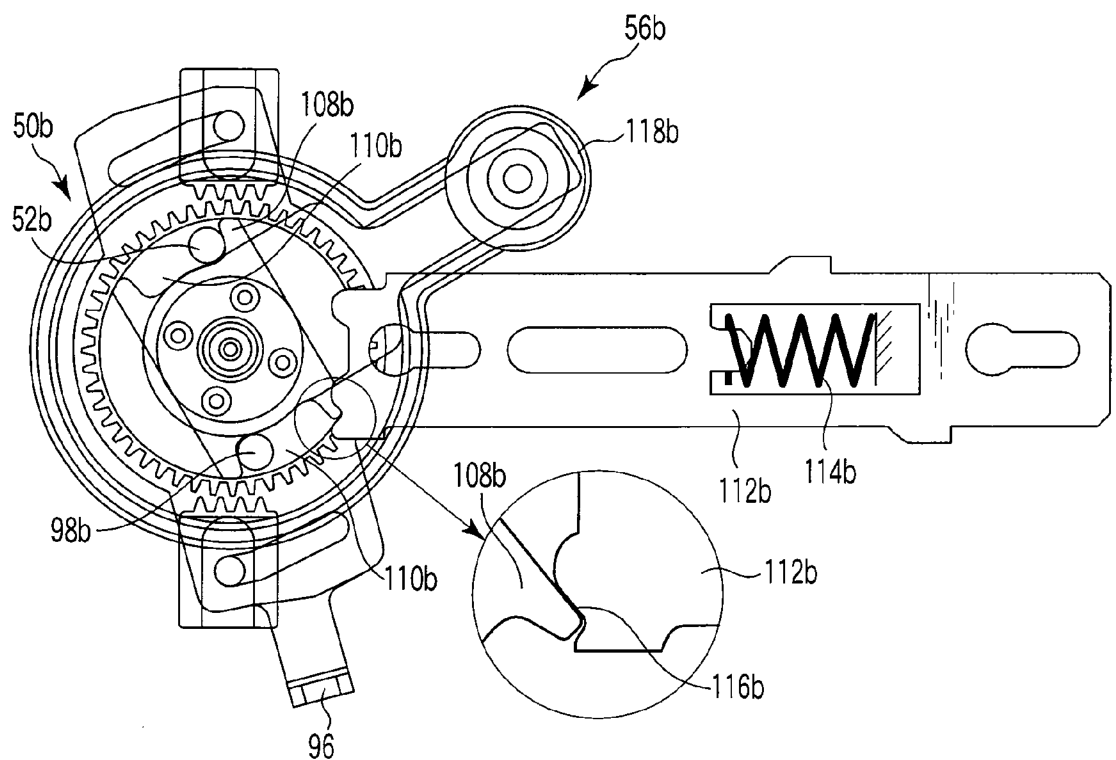
F I G. 13B

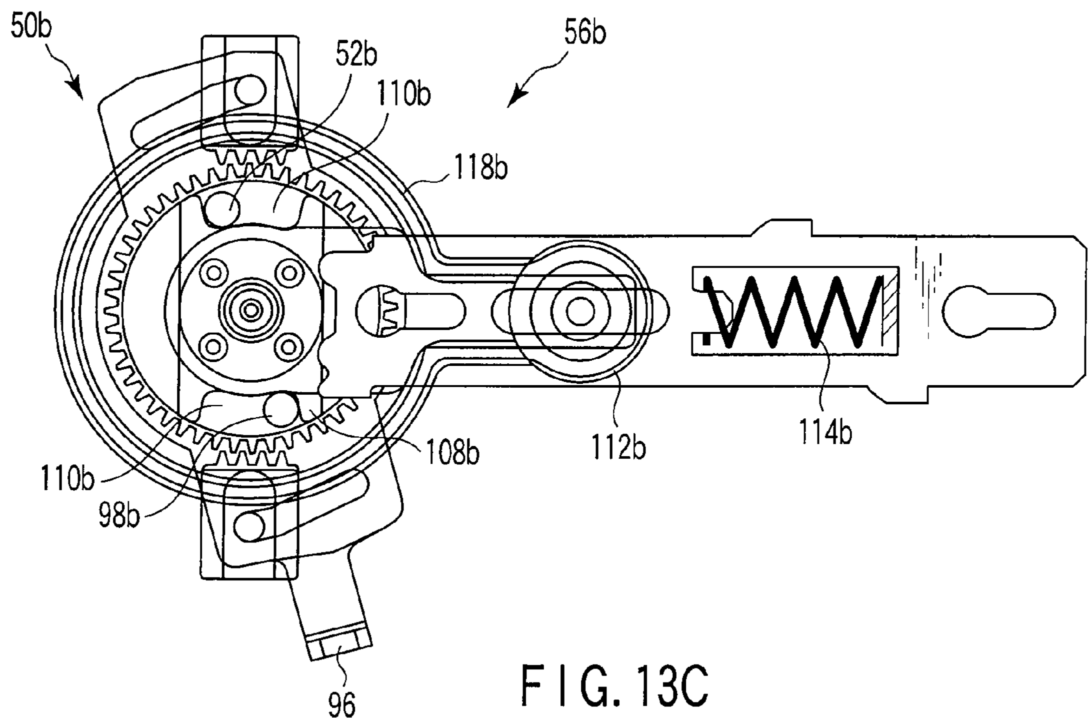
F I G. 13C
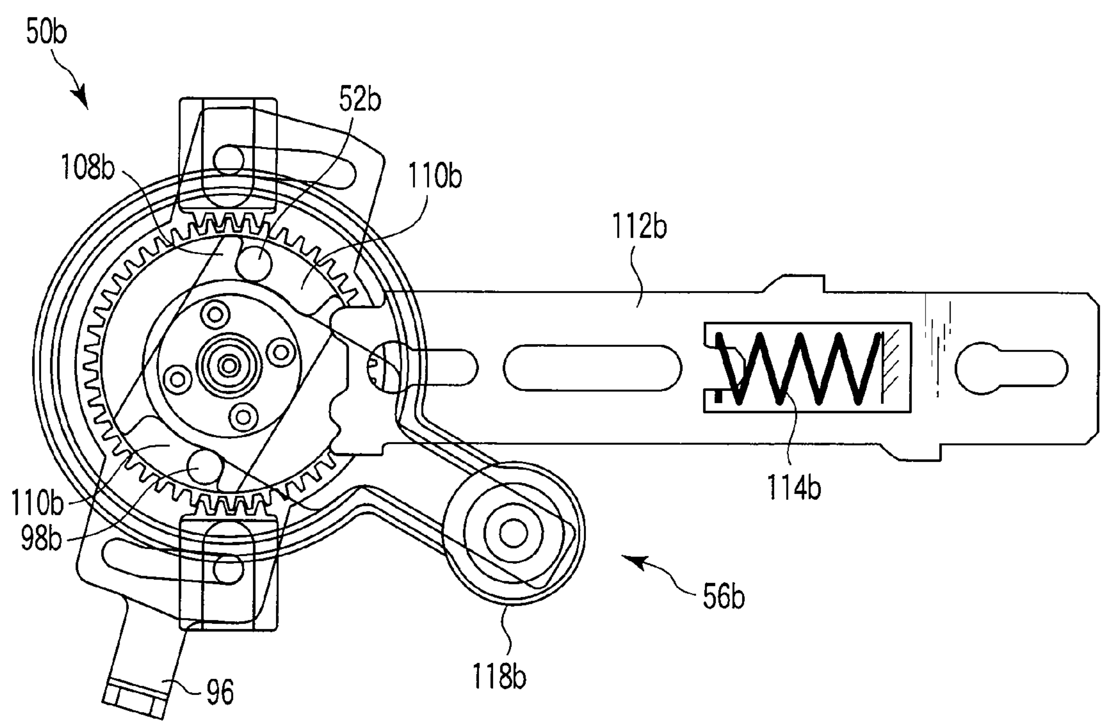
F I G. 13D

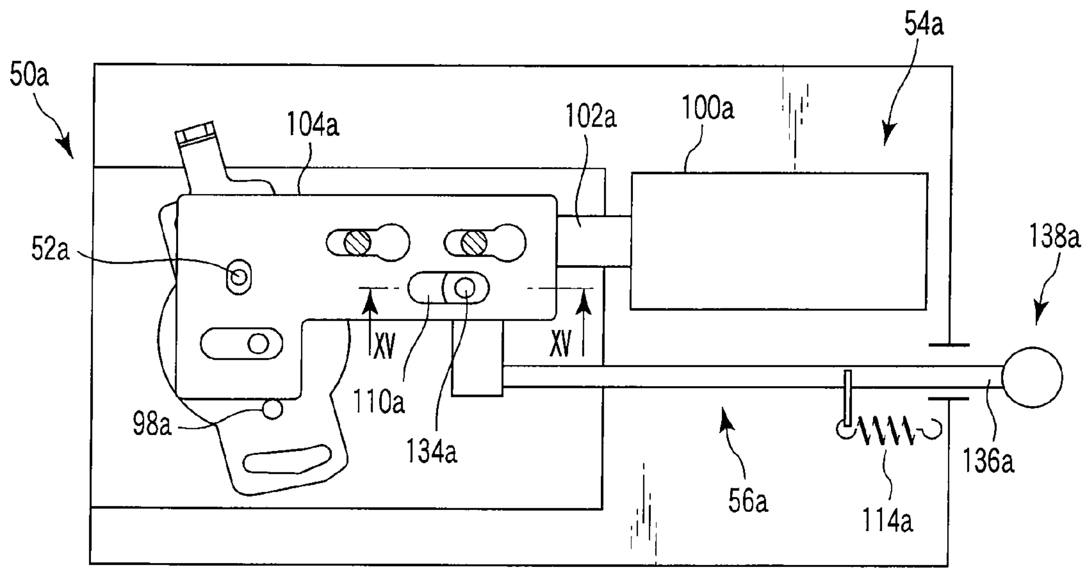
F I G. 14
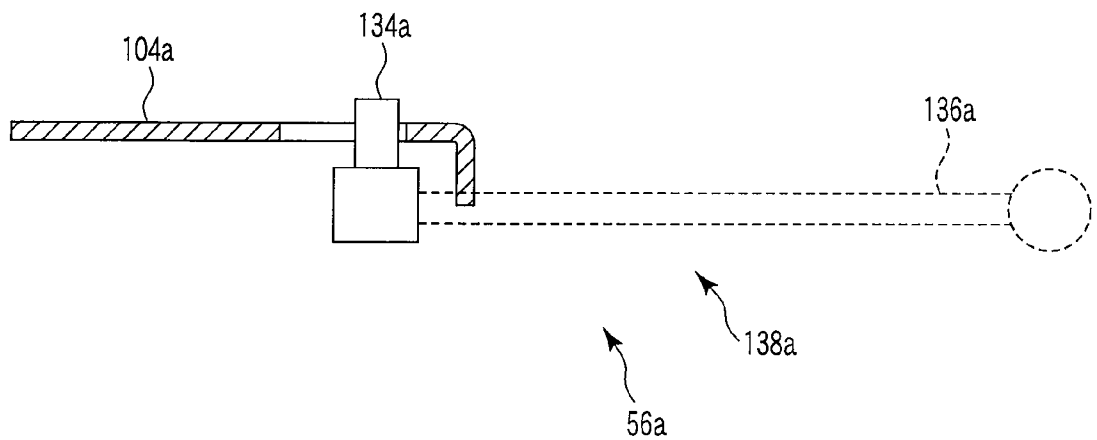
F I G. 15

POWER TRANSMISSION APPARATUS FOR ELECTRIC BENDING ENDOSCOPE

CROSS-REFERENCE TO RELATED APPLICATIONS

This application is based upon and claims the benefit of priority from prior Japanese Patent Application No. 2007-160502, filed Jun. 18, 2007, the entire contents of which are incorporated herein by reference.

BACKGROUND OF THE INVENTION

1. Field of the Invention

The present invention relates to a power transmission apparatus for an electric bending endoscope whose bending portion is to be electrically operated to be bent.

2. Description of the Related Art

In an electric bending endoscope, a bending portion to be operated to be bent is provided at the distal end portion of an elongate insertion portion to be inserted into a body cavity, and an operation portion to be held and operated by an operator is coupled to the proximal end portion of the insertion portion. The operation portion is provided with a bending switch and includes a motor and an angle mechanism therein, and an angle wire extending out of the angle mechanism is inserted through the insertion portion, and coupled to the distal end portion of the bending portion. When the bending switch is operated, the motor actuate the angle mechanism to move the angle wire back and forth, and so the bending portion is operated to be bent. Here, a clutch mechanism is provided between the motor and the angle mechanism. When the clutch mechanism is operated, the motor is separated from the angle mechanism, and the angle mechanism is free, and so the bending portion becomes linear easily. As such a clutch mechanism, Jpn. Pat. Appln. KOKAI Publication No. 5-95896 has disclosed a clutch mechanism to be actuated by manually operating an operation lever, and Jpn. Pat. Appln. KOKAI Publication No. 2003-275168 has disclosed a clutch mechanism to be actuated by an electric drive mechanism.

BRIEF SUMMARY OF THE INVENTION

In an aspect of the present invention, a power transmission apparatus for an electric bending endoscope includes: a power transmission mechanism to transmit power; a clutch mechanism switchable between a connection state to permit the transmission of the power by the power transmission mechanism and a release state not to permit the transmission of the power by the power transmission mechanism; an actuating member switchable between a connection position to bring the clutch mechanism into the connection state and a release position to bring the clutch mechanism into the release state, the actuating member being interlocked with the clutch mechanism; an electric drive mechanism electrically switchable between a connection drive state to bring the actuating member into the connection position and a release drive state to bring the actuating member into the release position, the electric drive mechanism being interlocked with the actuating member; and a manual drive mechanism including an operation member manually switchable to at least one of a connection drive position to bring the actuating member into the connection position and a release drive position to bring the actuating member into the release position, and a selective actuation transmission mechanism provided between the operation member and the actuating member and to transmit the actuation of the operation member to the actuating member and absorb the actuation of the actuating member without transmitting the actuation to the operation member.

In an aspect of the present invention, an electric bending endoscope includes a power transmission apparatus, the power transmission apparatus including: a power transmission mechanism to transmit power; a clutch mechanism switchable between a connection state to permit the transmission of the power by the power transmission mechanism and a release state not to permit the transmission of the power by the power transmission mechanism; an actuating member switchable between a connection position to bring the clutch mechanism into the connection state and a release position to bring the clutch mechanism into the release state, the actuating member being interlocked with the clutch mechanism; an electric drive mechanism electrically switchable between a connection drive state to bring the actuating member into the connection position and a release drive state to bring the actuating member into the release position, the electric drive mechanism being interlocked with the actuating member; and a manual drive mechanism including an operation member manually switchable to at least one of a connection drive position to bring the actuating member into the connection position and a release drive position to bring the actuating member into the release position, and a selective actuation transmission mechanism provided between the operation member and the actuating member and to transmit the actuation of the operation member to the actuating member and absorb the actuation of the actuating member without transmitting the actuation to the operation member.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing an endoscope system in a first embodiment of the present invention;

FIG. 2 is a schematic diagram showing a power transmission apparatus in the first embodiment of the present invention;

FIG. 3 is a schematic diagram showing the power transmission apparatus in the first embodiment of the present invention along the III-III line in FIG. 2;

FIG. 5 is a perspective view showing a pair of clutch mechanisms in the first embodiment of the present invention;

FIG. 6 is a side view showing an electric drive mechanism in the first embodiment of the present invention;

FIG. 10 is a sectional view showing the manual lever of the manual drive mechanism in the first embodiment of the present invention;

FIG. 11 is a perspective view showing a motor unit in the first embodiment of the present invention;

FIG. 13A is a schematic diagram showing the state of the clutch mechanism before released by the manual drive mechanism in the power transmission apparatus in the first embodiment of the present invention;

FIG. 13B is a schematic diagram showing the release state of the clutch mechanism by the manual drive mechanism in the power transmission apparatus in the first embodiment of the present invention;

FIG. 13C is a schematic diagram showing the state of the clutch mechanism before connected by the manual drive mechanism in the power transmission apparatus in the first embodiment of the present invention;

FIG. 13D is a schematic diagram showing the connection state of the clutch mechanism by the manual drive mechanism in the power transmission apparatus in the first embodiment of the present invention;

FIG. 14 is a side view showing a power transmission mechanism in a second embodiment of the present invention; and FIG. 15 is a sectional view showing a power transmission mechanism in the second embodiment of the present invention along the XV-XV line in FIG. 14.

DETAILED DESCRIPTION OF THE INVENTION

Figure 4A:
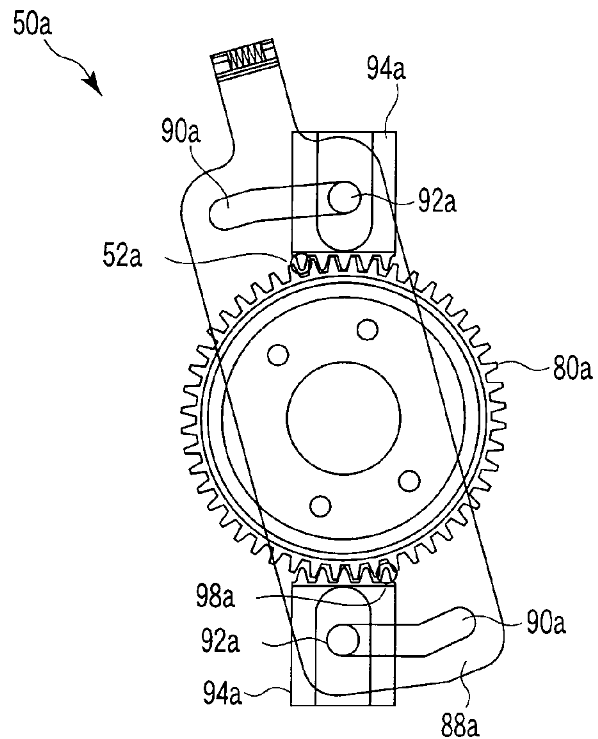
FIG. 4A is a schematic diagram showing a clutch mechanism in a connection state in the first embodiment of the present invention.
Figure 4B:
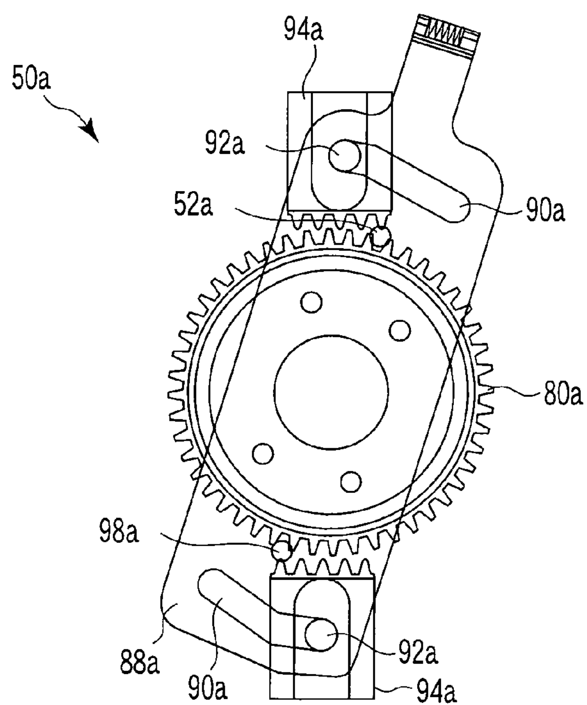
FIG. 4B is a schematic diagram showing the clutch mechanism in a release state in the first embodiment of the present invention.

Embodiments of the present invention will hereinafter be described with reference to the drawings.

FIGS. 1 to 13D show a first embodiment of the present invention.

The schematic configuration of an endoscope system is explained with reference to FIG. 1.

An electric bending endoscope 20 (hereinafter simply referred to as an endoscope 20) of the endoscope system includes an elongate insertion portion 22 to be inserted into a body cavity. A bending portion 24 to be bent in four directions, that is, in up, down, left and right directions is provided at the distal end portion of the insertion portion 22, and an insertion and removal portion 26 is provided at the proximal end portion of the insertion portion 22. Here, the insertion and removal portion 26 includes an angle mechanism therein, and an angle wire extending out of the angle mechanism is inserted through the insertion portion 22, and coupled to the distal end portion of the bending portion 24. Further, the insertion and removal portion 26 is removably inserted into a motor unit 28, and a drive apparatus for actuating the angle mechanism is provided in the motor unit 28. As described later, a clutch mechanism is provided in a power transmission apparatus of the drive apparatus. The motor unit 28 is held by a holding apparatus 30 such that the motor unit 28 is movable and fixable, and rotatable about its central axis. Moreover, the motor unit 28 is connected to a video processor 34 via a universal cord 32, and an operation portion 38 to be held and operated by an operator is connected to the video processor 34 via an electric cord 36. The operation portion 38 is provided with a bending switch 40 and a changeover switch 42. When the bending switch 40 is operated, the angle mechanism is actuated by the drive apparatus of the motor unit 28, the angle wire is moved back and forth, and so the bending portion 24 is bent. When the changeover switch 42 is operated, the clutch mechanism of the power transmission apparatus of the drive apparatus is switched.

The drive apparatuses 44*a*, 44*b* of the motor unit 28 are explained with reference to FIGS. 2 to 11.

Figure 9:
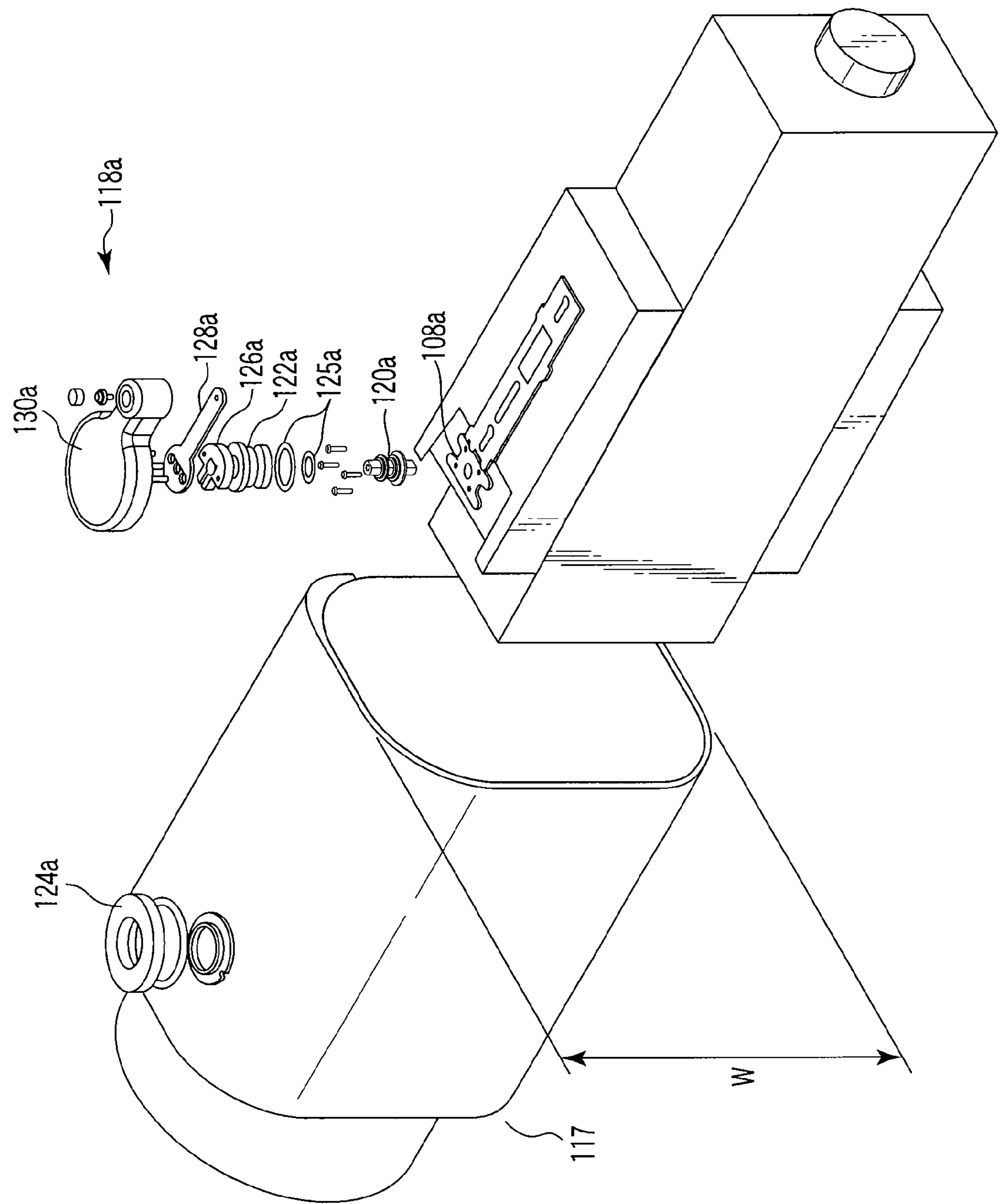
FIG. 9 is an exploded perspective view showing a manual lever of the manual drive mechanism in the first embodiment of the present invention.

Referring to FIG. 9, in the motor unit 28, a rectangular cylindrical frame 60 extends along the central axis of the motor unit 28, and the first and second drive apparatuses 44*a*, 44*b* are provided outside two opposite sidewalls of the frame 60, respectively. It is to be noted that in the present specification, the first drive apparatus and its components are indicated with a reference mark Xa, while the second drive apparatus and its components are indicated with a reference mark Xb. One of the drive apparatuses is used for up-down direction bending operation, and the other drive apparatus is used for left-right direction bending operation. The two drive apparatuses 44*a*, 44*b* include the same configuration, and are arranged in rotational symmetry with respect to the central axis of the motor unit 28.

A power transmission apparatus 46*a*, 46*b* of the drive apparatus 44*a*, 44*b* is formed of a power transmission mechanism 48*a*, 48*b*, a clutch mechanism 50*a*, 50*b*, a drive pin 52*a*, 52*b* as actuating member, a electric drive mechanism 54*a*, 54*b*, and a manual drive mechanism 56*a*, 56*b*, which will be sequentially explained below.

The power transmission mechanism 48*a*, 48*b* is explained with reference to FIGS. 2 and 3.

A drive shaft of motor 58*a*, 58*b* is connected to an output shaft 86*a*, 86*b* at a reduction ratio via a gear train in a gear unit 59*a*, 59*b*. Here, a fixing gear 80*a*, 80*b* as an annular gear are interposed between the gear train. The fixing gear 80*a*, 80*b* is switchable between a fixing state unrotatable on its central axis and a fixing-released state rotatable. In the case where the fixing gear 80*a*, 80*b* is in the fixing state, when the drive shaft of the motor 58*a*, 58*b* is rotated, the gear train is sequentially rotated and so the output shaft 86*a*, 86*b* is rotated at a reduced rotation velocity. On the other hand, in the case where the fixing gear 80*a*, 80*b* is in the fixing-released state, even when the drive shaft of the motor 58*a*, 58*b* are rotated, the gear train idle and rotation torque is not transmitted to the output shaft 86*a*, 86*b*.

The clutch mechanism 50*a*, 50*b* of the power transmission mechanism 48*a*, 48*b* is explained with reference to FIGS. 2 to 5.

The outer peripheral portion of the fixing gear 80*a*, 80*b* form spur gear, and external teeth are formed on the fixing gear 80*a*, 80*b*. Cam 88*a*, 88*b* is provided axially outside the fixing gear 80*a*, 80*b* and rotatable about a rotational axis coaxial with the central axis of the fixing gear 80*a*, 80*b* between a connection position and a release position. Cam grooves 90*a*, 90*b* extend in rotational symmetry at both ends of the cam 88*a*, 88*b*. A cam pin 92*a*, 92*b* are slidably inserted into the cam groove 90*a*, 90*b*, and project from limitation member 94*a*, 94*b*. The limitation member 94*a*, 94*b* is unrotatable in a circumferential direction of the central axis of the fixing gear 80*a*, 80*b* and slidable in a radial direction thereof with respect to the fixing gear 80*a*, 80*b*. By the interaction between the cam groove 90*a*, 90*b* and the cam pin 92*a*, 92*b*, the limitation member 94*a*, 94*b* is disposed at a radially inward connection position when the cam 88*a*, 88*b* is disposed at the connection position while the limitation member 94*a*, 94*b* is disposed at a radially outward release position when the cam 88*a*, 88*b* is disposed at the release position.

Teeth to gear with the external teeth of the fixing gear 80*a*, 80*b* are formed in the limitation member 94*a*, 94*b*. When the limitation member 94*a*, 94*b* is at the connection position, the teeth of the limitation member 94*a*, 94*b* gear with the external teeth of the fixing gear 80*a*, 80*b*, and the fixing gear 80*a*, 80*b* is at the unrotatable fixed state by the circumferentially unrotatable limitation member 94*a*, 94*b*. On the other hand, when the limitation member 94*a*, 94*b* is at the release position, the teeth of the limitation member 94*a*, 94*b* is separated from the external teeth of the fixing gear 80*a*, 80*b*, and the fixing gear 80*a*, 80*b* is at the rotatable fixing-released state. When the fixing gear 80*a*, 80*b* is in the fixing state, the transmission of power by the power transmission mechanism 48*a*, 48*b* is possible. This is the connection state of the clutch mechanism 50*a*, 50*b* (see FIG. 4A). When the fixing gear 80*a*, 80*b* is in the fixing-released state, the respective gear idles, and so the transmission of power by the power transmission mechanism 48*a*, 48*b* is impossible. This is the release state of the clutch mechanism 50*a*, 50*b* (see FIG. 4B).

The first cam 88*a* of the first clutch mechanism 50*a* and the second cam 88*b* of the second clutch mechanism 50*b* are coupled to each other by a coupling beam 96 as a coupling mechanism extending to traverse the frame 60. Owing to the coupling beam 96, the second cam 88*b* is also disposed at the connection position when the first cam 88*a* is disposed at the connection position, and the second cam 88*b* is also disposed at the release position when the first cam 88*a* is disposed at the release position. Thus, the first and second clutch mechanisms 50*a*, 50*b* are interlocked with each other.

The drive pin 52*a*, 52*b* as the actuating member to be interlocked with the clutch mechanism 50*a*, 50*b* is explained with reference to FIGS. 4A to 5.

The drive pin 52*a*, 52*b* and limitation pin 98*a*, 98*b* protrude axially outwardly from the cam 88*a*, 88*b*, and are arranged in symmetry with respect to the rotational axis on the center line of the cam 88*a*, 88*b*. The first drive pin 52*a* is disposed in proximity to the coupling beam 96 in the first cam 88*a*, while the second drive pin 52*b* is disposed separately from the coupling beam 96 in the second cam 88*b*. The drive pin 52*a*, 52*b* and the clutch mechanism 50*a*, 50*b* are interlocked with each other. That is, the drive pin 52*a*, 52*b* is switched between a connection position and a release position so that the clutch mechanism 50*a*, 50*b* is switched between the connection state and the release state, and the clutch mechanism 50*a*, 50*b* is switched between the connection state and the release state so that the drive pin 52*a*, 52*b* is switched between the connection position and the release position.

Figure 7:
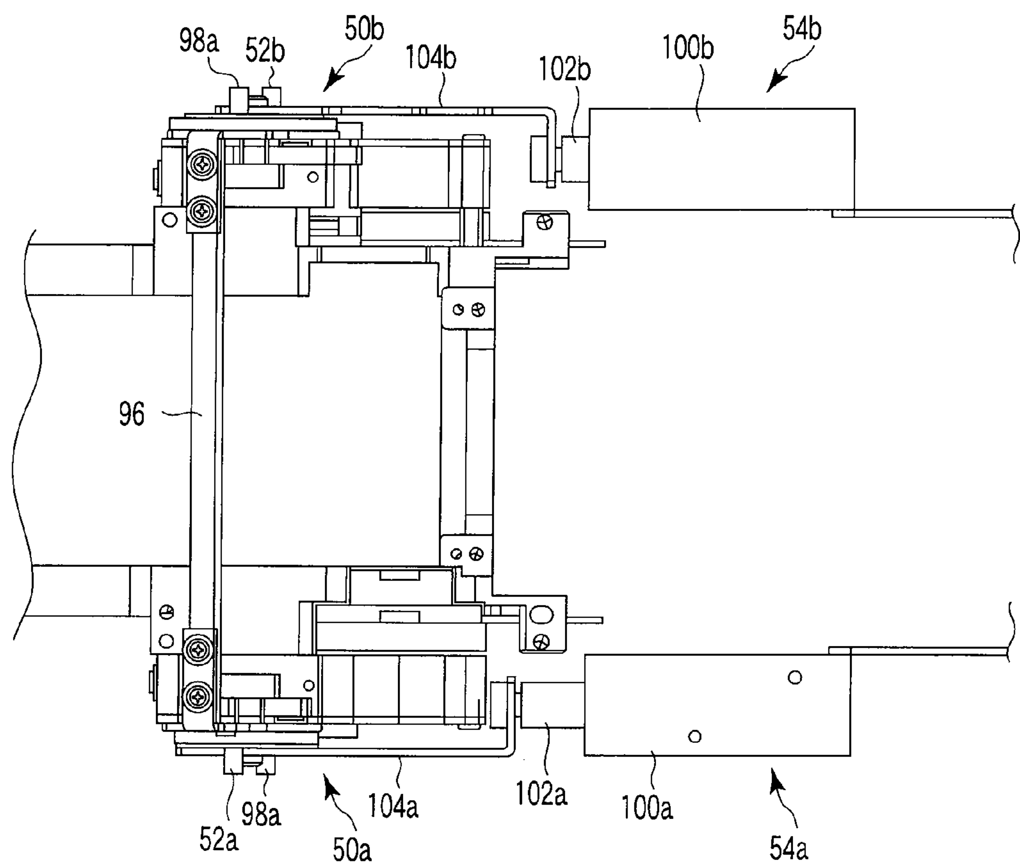
FIG. 7 is a top view showing the electric drive mechanism in the first embodiment of the present invention.

The electric drive mechanism 54*a*, 54*b* for electrically actuating the clutch mechanism 50*a*, 50*b* is explained with reference to FIGS. 5 to 7.

In the electric drive mechanism 54*a*, 54*b*, a solenoid 100*a*, 100*b* is arranged on the proximal side of the clutch mechanism 50*a*, 50*b* in the direction of the central axis of the motor unit 28. One end of sliding member 104*a*, 104*b* is coupled to an iron core 102*a*, 102*b* of the solenoid 100*a*, 100*b*, and the iron core 102*a*, 102*b* and the sliding member 104*a*, 104*b* is movable back and forth along guide pin 106*a*, 106*b*. At the other end of the sliding member 104*a*, 104*b*, the drive pin 52*a*, 52*b* is coupled to the sliding member 104*a*, 104*b* rotatably about its central axis. The direction of the back-and-forth movement of the iron core 102*a*, 102*b* and the sliding member 104*a*, 104*b* and the rotating direction of the drive pin 52*a*, 52*b* substantially coincide with each other and are substantially parallel with the direction of the central axis of the motor unit 28. When the iron core 102*a*, 102*b* and the sliding member 104*a*, 104*b* is moved back and forth by the solenoid 100*a*, 100*b*, the drive pin 52*a*, 52*b* is rotated and so the clutch mechanism 50*a*, 50*b* is actuated.

The solenoid 100*a*, 100*b* take an attraction state and a reset state, and can only be actuated from the attraction state to the reset state, and the solenoid 100*a*, 100*b* is a self-holding type such that the attraction state is a hold state and the reset state is an open state when electricity is turned off. When the solenoid 100*a*, 100*b* is in the attraction state or the reset state, the sliding member 104*a*, 104*b* is disposed at a backward position or a forward position. Here, the first drive pin 52*a* and the second drive pin 52*b* are disposed in rotational symmetry to each other with respect to a common rotational axis, and so the second solenoid 100*b* is in the reset state or attraction state when the first solenoid 100*a* is in the attraction state or the reset state so that the second sliding member 104*b* is disposed at the forward position or backward position when the first sliding member 104*a* is at the backward position or forward position.

When the second solenoid 100*b* is held in the attraction state, the second sliding member 104*b* is held at the backward position, the second drive pin 52*b* is held at the connection position, the second clutch mechanism 50*b* is held in the connection state, and the first clutch mechanism 50*a* is held in the connection state via the coupling beam 96. This is the connection drive state of the electric drive mechanism 54*a*, 54*b*. On the other hand, when the first solenoid 100*a* is in the attraction state, the first sliding member 104*a* is held at the backward position, the first drive pin 52*a* is held at the release position, the clutch mechanism 50*a* is held at the release state, and the second clutch mechanism 50*b* is held in the release state via the coupling beam 96. This is the release drive state of the electric drive mechanism 54*a*, 54*b*.

The manual drive mechanism 56*a*, 56*b* for manually actuating the clutch mechanism 50*a*, 50*b* is explained with reference to FIGS. 8 to 11.

Figure 8:
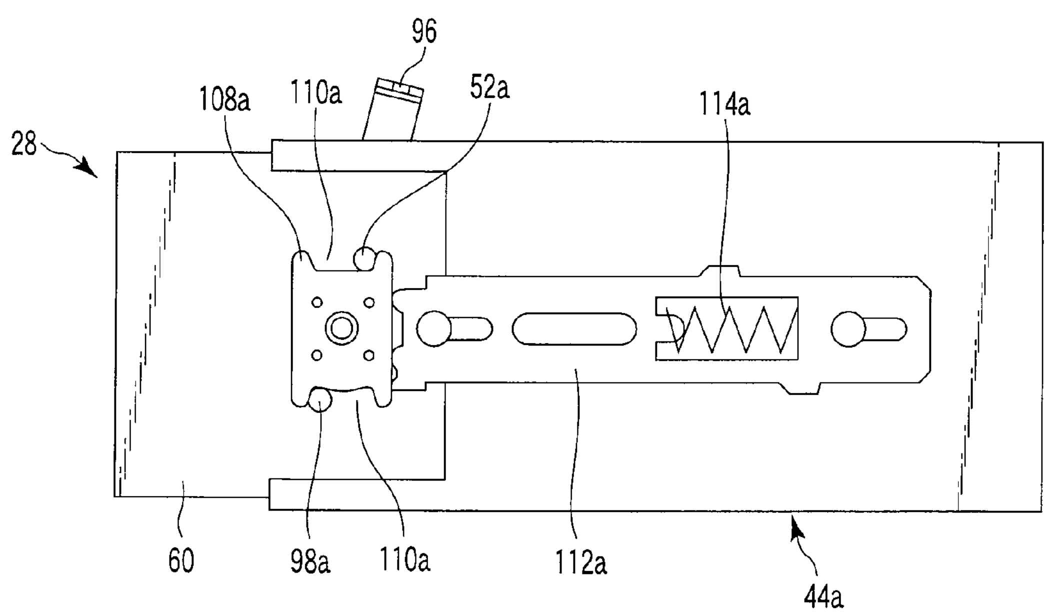
FIG. 8 is a side view showing a selective actuation transmission mechanism of a manual drive mechanism in the first embodiment of the present invention.

Referring to FIG. 8, a selector 108*a*, 108*b* as a selection member are provided axially outside the cam 88*a*, 88*b*. The selector 108*a*, 108*b* is rotatable about a rotational axis coaxial with the rotational axis of the cam 88*a*, 88*b* with reference to a neutral position between a connection position and a release position. A pair of play portions 110*a*, 110*b* in the shape of notched grooves is formed in the selector 108*a*, 108*b*. When the selector 108*a*, 108*b* is at the neutral position, the drive pin 52*a*, 52*b* and the limitation pin 98*a*, 98*b* of the cam 88*a*, 88*b* are rotatable in the pair of play portions 110*a*, 110*b* without interfering with the selector 108*a*, 108*b*. When the selector 108*a*, 108*b* rotates from the neutral position, the drive pin 52*a*, 52*b* and the limitation pin 98*a*, 98*b* are rotated by the selectors 108*a*, 108*b*, and the drive pin 52*a*, 52*b* is disposed at the connection position When the selector 108*a*, 108*b* is at the connection position and the drive pin 52*a*, 52*b* is disposed at the release position When the selector 108*a*, 108*b* is at the release position. An urging member 112*a*, 112*b* is provided side by side with the selector 108*a*, 108*b*. The urging member 112*a*, 112*b* urge the selector 108*a*, 108*b* by the elastic force of an elastic member 114*a*, 114*b* and thus hold the selector 108*a*, 108*b* at the neutral position. Moreover, an engaging portion 116*a*, 116*b* is formed at the end of the urging member 112*a*, 112*b* on the side of the selector 108*a*, 108*b* and the engaging portion 116*a*, 116*b* engages with and hold the selector 108*a*, 108*b* when the selector 108*a*, 108*b* is disposed at the release position.

Referring to FIGS. 9 and 10, a manual lever 118*a*, 118*b* as an operation member is coupled to the selector 108*a*, 108*b*. That is, a lever shaft 120*a*, 120*b* is axially outwardly coupled to the selector 108*a*, 108*b* by screws coaxially with the selector 108*a*, 108*b*. An annular shaft guide 122*a*, 122*b* is fitted coaxially outside the lever shaft 120*a*, 120*b*. Here, an annular lever bearing 124*a*, 124*b* is provided coaxially with the lever shaft 120*a*, 120*b* in a housing 117 of the motor unit 28, and the shaft guide 122*a*, 122*b* is fitted coaxially into the lever bearing 124*a*, 124*b*. O-rings 125*a*, 125*b* are interposed between the lever shaft 120*a*, 120*b* and the shaft guide 122*a*, 122*b* and between the shaft guide 122*a*, 122*b* and the lever bearing 124*a*, 124*b*, respectively. A clamp member 126*a*, 126*b* is fitted outside the lever shaft 120*a*, 120*b* axially outside the shaft guide 122*a*, 122*b*. The proximal end portion of a lever member 128*a*, 128*b* is coupled by a screw to the lever shaft 120*a*, 120*b* and the clamp member 126*a*, 126*b*, and the lever member 128*a*, 128*b* extend perpendicularly to the lever shaft 120*a*, 120*b*. A lever cover 130*a*, 130*b* covers the lever member 128*a*, 128*b*. In addition, a claw portion 132*a*, 132*b* is formed at the proximal end portion of the lever cover 130*a*, 130*b*, and the claw portion 132*a*, 132*b* are engaged with the clamp member 126*a*, 126*b* and so the proximal end portion of the lever cover 130*a*, 130*b* is fixed to the clamp member 126*a*, 126*b*. On the other hand, the terminal end of the lever cover 130*a*, 130*b* is fixed to the terminal end of the lever member 128*a*, 128*b* by a screw.

The manual lever 118*a*, 118*b* is rotatable with reference to a neutral position between a connection drive position and a release drive position. When the manual lever 118*a*, 118*b* is disposed at the connection position, release position or neutral position, the selector 108*a*, 108*b* is disposed at the connection position, release position or neutral position.

Referring to FIG. 11, the pair of manual levers 118*a*, 118*b* is arranged in rotational symmetry with respect to the central axis of the motor unit 28 on both sides of the motor unit 28.

Next, the actuation of a selective actuation transmission mechanism of the power transmission apparatus 46*a*, 46*b* will be described.

Figure 12A:
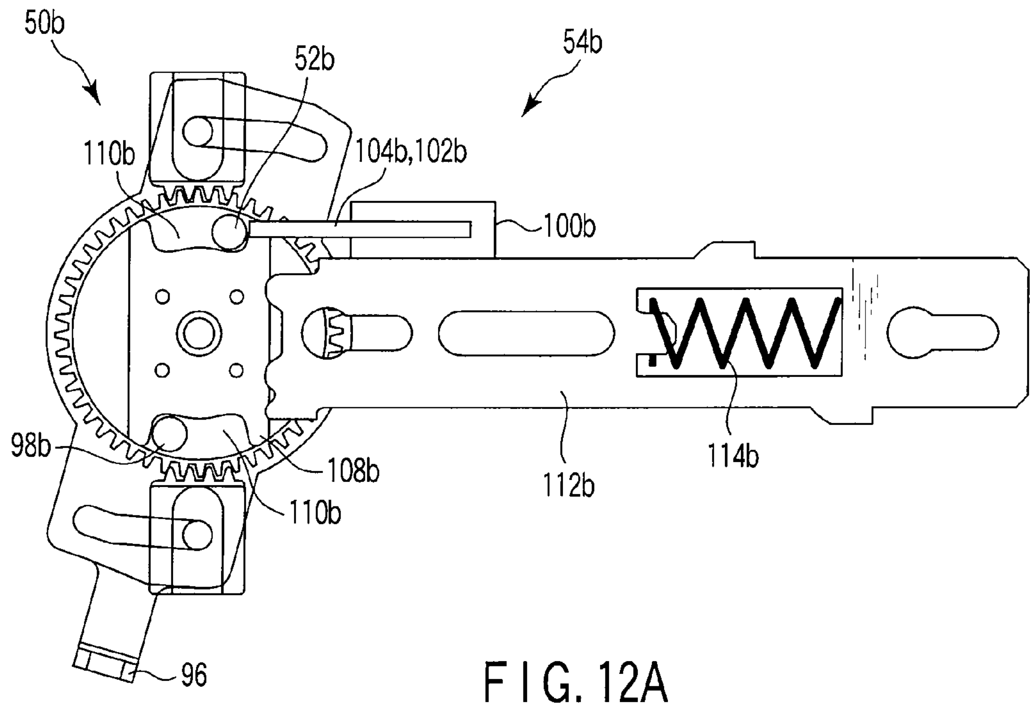
FIG. 12A is a schematic diagram showing the connection state of the clutch mechanism by the electric drive mechanism in the power transmission apparatus in the first embodiment of the present invention.
Figure 12B:
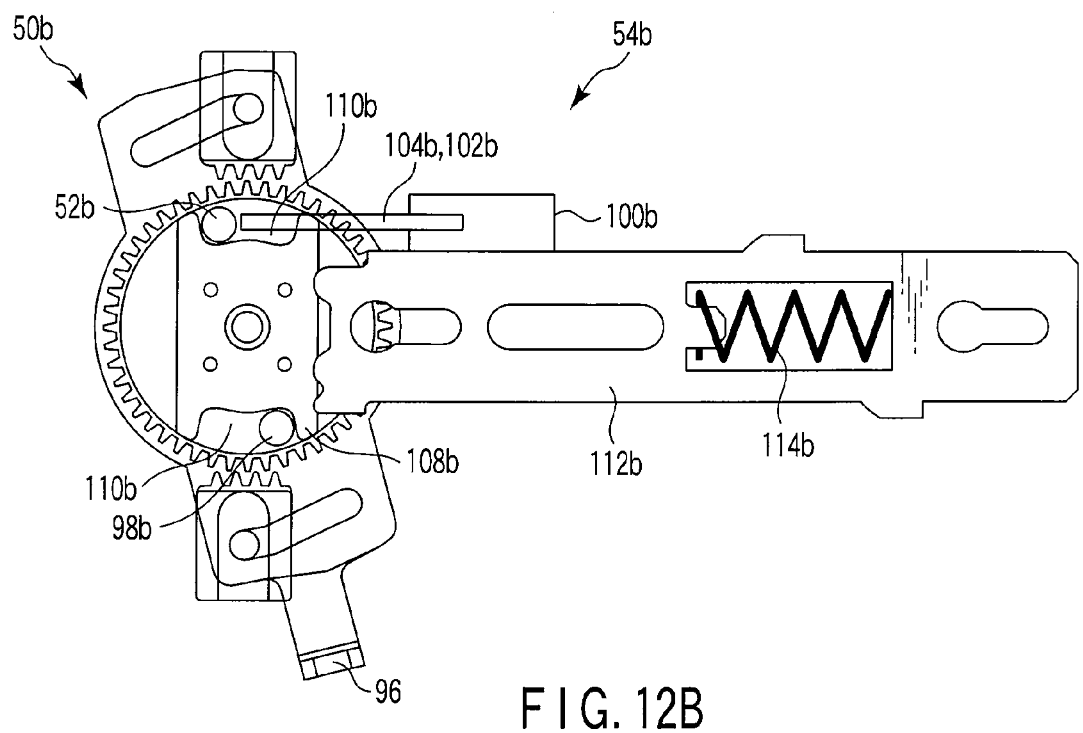
FIG. 12B is a schematic diagram showing the release state of the clutch mechanism by the electric drive mechanism in the power transmission apparatus in the first embodiment of the present invention.

Referring to FIGS. 12A and 12B, the switching of the first and second clutch mechanisms 50*a*, 50*b* by the electric drive mechanism 54*a*, 54*b* are explained.

When the manual lever 118*a*, 118*b* is not operated, the manual lever 118*a*, 118*b* and the selector 108*a*, 108*b* are held at the neutral position by the urging member 112*a*, 112*b*.

When the changeover switch 42 of the operation portion 38 is operated and so a signal for switching from the connection state to the release state is input to the electric drive mechanism 54*a*, 54*b*, the second solenoid 100*b* is switched from the attraction state to the reset state. As a result, from the state shown in FIG. 12A to the state shown in FIG. 12B, the second sliding member 104*b* is switched from the backward position to the forward position, the second drive pin 52*b* is switched from the connection position to the release position, the second clutch mechanism 50*b* is switched from the connection state to the release state, the first clutch mechanism 50*a* is switched from the connection state to the release state via the coupling beam 96, the first drive pin 52*a* is switched from the connection position to the release position, the first sliding member 104*a* is switched from the forward position to the backward position, and the first solenoid 100*a* is switched from the reset state to the attraction state.

On the other hand, when the changeover switch 42 of the operation portion 38 is operated and so a signal for switching from the release state to the connection state is input to the electric drive mechanism 54*a*, 54*b*, the first solenoid 100*a* is switched from the attraction state to the reset state. As a result, from the state shown in FIG. 12B to the state shown in FIG. 12A, the first sliding member 104*a* is switched from the backward position to the forward position, the first drive pin 52*a* is switched from the release position to the connection position, the first clutch mechanism 50*a* is switched from the release state to the connection state, the second clutch mechanism 50*b* is switched from the release state to the connection state via the coupling beam 96, the second drive pin 52*b* is switched from the release position to the connection position, the second sliding member 104*b* is switched from the backward position to the forward position, and the second solenoid 100*b* is switched from the reset state to the attraction state.

In any one of the switching operations, the selector 108*a*, 108*b* is not actuated by the actuation of the drive pin 52*a*, 52*b* owing the function of play formed between the drive pin 52*a*, 52*b* and the selector 108*a*, 108*b*, and the actuation is not transmitted from the drive pin 52*a*, 52*b* to the manual lever 118*a*, 118*b* via the selector 108*a*, 108*b*. That is, the actuation is not transmitted from the electric drive mechanism 54*a*, 54*b* to the manual lever 118*a*, 118*b*.

Referring to FIGS. 13A to 13D, the switching of the first and second clutch mechanisms 50*a*, 50*b* by the manual drive mechanism 56*a*, 56*b* are explained.

In the case where the first and second clutch mechanisms 50*a*, 50*b* are in the connection state, when the second manual lever 118*b*, for example, is switched from the neutral position to the release position, from the state shown in FIG. 13A to the state shown in FIG. 13B, the second selector 108*b* is switched from the neutral position to the release position and the second drive pin 52*b* is switched from the connection position to the release position by the second selector 108*b*. Due to the switching of the second drive pin 52*b*, the second clutch mechanism 50*b* is switched from the connection state to the release state, the second sliding member 104*b* is switched from the backward position to the forward position, and the second solenoid 100*b* is switched from the attraction state to the reset state. Here, as the second solenoid 100*b* is a self-holding type such that the attraction state is held, a sense of click is produced in the operation of the second manual lever 118*b*. Further, owing to the coupling beam 96, the first clutch mechanism 50*a* is switched from the connection state to the release state, and the first drive pin 52*a* is switched from the connection position to the release position. Although the first sliding member 104*a* is switched from the forward position to the backward position and the first solenoid 100*a* is switched from the reset state to the attraction state by the switching of the first drive pin 52*a*, the first selector 108*a* is at the neutral position and is thus not actuated by the first drive pin 52*a*, and so the first manual lever 118*a* is not actuated and held at the neutral position. In addition, as shown in FIG. 13B in a magnified form, when the second selector 108*b* is switched from the neutral position to the release position, the second selector 108*b* is engaged with and held by the second engaging portion 116*b* of the second urging member 112*b*, and so the second manual lever 118*b* is held at the release position. Therefore, the state of the second clutch mechanism 50*b* can be judged from the position of the second manual lever 118*b*. The actuation described above concerns a case where the second manual lever 118*b* is switched, and also holds true with a case where the first manual lever 118*a* is switched.

In the case where the first and second clutch mechanisms 50*a*, 50*b* are in the release state, when the second manual lever 118*b*, for example, is switched from the neutral position to the connection position, from the state shown in FIG. 13C to the state shown in FIG. 13D, the second selector 108*b* is switched from the neutral position to the connection position and the second drive pin 52*b* is switched from the release position to the connection position by the second selector 108*b*. Due to the switching of the second drive pin 52*b*, the second clutch mechanism 50*b* is switched from the release state to the connection state, the second sliding member 104*b* is switched from the forward position to the backward position, and the second solenoid 100*b* is switched from the reset state to the attraction state. Further, owing to the coupling beam 96, the first clutch mechanism 50*a* is switched from the release state to the connection state, and the first drive pin 52*a* is switched from the release position to the connection position. Although the first sliding member 104*a* is switched from the backward position to the forward position and the first solenoid 100*a* is switched from the attraction state to the reset state by the switching of the first drive pin 52*a*, the first selector 108*a* is at the neutral position and is thus not actuated by the first drive pin 52*a*, and so the first manual lever 118*a* is not actuated and held at the neutral position. Here, as the first solenoid 100*a* is a self-holding type such that the attraction state is held, a sense of click is produced in the operation of the second manual lever 118*b*. In addition, when the operation of the second manual lever 118*b* is released, the second selector 108*b* is reset to the neutral position by the second urging member 112*b*, and the second manual lever 118*b* is reset to the neutral position. The actuation described above concerns a case where the second manual lever 118*b* is switched, and also holds true with a case where the first manual lever 118*a* is switched.

In any one of the switching operations, the actuation is transmitted from the manual lever 118*a*, 118*b* to the drive pin 52*a*, 52*b* via the selector 108*a*, 108*b*, and the electric drive mechanism 54*a*, 54*b* is actuated by the actuation of the drive pin 52*a*, 52*b*. That is, the actuation is transmitted from the manual lever 118*a*, 118*b* to the electric drive mechanism 54*a*, 54*b*.

Therefore, the power transmission apparatus 46*a*, 46*b* in the present embodiment includes the following effects.

In the power transmission apparatus 46*a*, 46*b* in the present embodiment, even when the drive pin 52*a*, 52*b* is actuated by the electric drive mechanism 54*a*, 54*b*, the actuation is not transmitted from the drive pin 52*a*, 52*b* to the manual lever 118*a*, 118*b* via the selector 108*a*, 108*b* owing to the play provided between the drive pin 52*a*, 52*b* and the selector 108*a*, 108*b* as long as the manual lever 118*a*, 118*b* are disposed at the neutral position. Thus, the actuation is not transmitted from the electric drive mechanism 54*a*, 54*b* to the manual lever 118*a*, 118*b*, and so output necessary for the electric drive mechanism 54*a*, 54*b* is reduced as compared with the case where the manual lever 118*a*, 118*b* is actuated by the actuation of the electric drive mechanism 54*a*, 54*b*, thereby enabling a size reduction of the electric drive mechanism 54*a*, 54*b* and the power transmission apparatus 46*a*, 46*b*. Moreover, the first and second clutch mechanisms 50*a*, 50*b* can be switched in conjunction with each other.

Since the solenoid 100*a*, 100*b* are only actuated from the attraction state to the reset state, the configuration of the solenoid 100*a*, 100*b* is simplified, and the solenoid 100*a*, 100*b* can be reduced in size. Moreover, it is not necessary to turn on electricity to hold the solenoid 100*a*, 100*b* in the attraction state, and so the power consumption of the solenoid 100*a*, 100*b* can be reduced.

Since the pair of drive apparatuses 44*a*, 44*b* is arranged in rotational symmetry with respect to the central axis of the motor unit 28, the center of gravity of the pair of drive apparatuses 44*a*, 44*b* is located on the central axis of the motor unit 28, and so the motor unit 28 is easily operated when rotated about its central axis.

As the claw portion 132*a*, 132*b* of the lever cover 130*a*, 130*b* is engaged with and the proximal end portion of the lever cover 130*a*, 130*b* is fixed to the clamp member 126*a*, 126*b*, there is no need for a screw to fix the proximal end portion of the lever cover 130*a*, 130*b*, and so the number of parts can be reduced.

When the motor unit 28 is assembled, as the manual lever 118*a*, 118*b* is attached after the housing 117 is attached and the manual lever 118*a*, 118*b* can be disposed outside the housing 117, and the width W of the housing 117 between the pair of manual levers 118*a*, 118*b* can be reduced and so the motor unit 28 can be reduced in size.

The two clutch mechanisms 50*a*, 50*b* can be switched by operation of one of the manual levers 118*a*, 118*b* and the pair of manual levers 118*a*, 118*b* is arranged in rotational symmetry with respect to the central axis of the motor unit 28, and so it is possible to easily access the manual levers 118*a*, 118*b* even when the motor unit 28 is rotated about its central axis.

FIGS. 14 and 15 show a second embodiment of the present invention.

The present embodiment is only different from the first embodiment in the configuration of the manual drive mechanism 56*a*.

The manual drive mechanism 56*a* is only provided in the first power transmission apparatus 46*a*. The play portion 110*a* in the shape of a long hole extends in the sliding member 104*a* as both the actuating member and the selection member in the direction of the back-and-forth movement of the sliding member 104*a*. An operation pin 134*a* is inserted through the play portion 110*a* perpendicularly to the direction of the back-and-forth movement of the sliding member 104*a*. One end of an operation rod 136*a* is coupled to the operation pin 134*a*, and the operation rod 136*a* extends in the direction of the back-and-forth movement of the sliding member 104*a*, while the other end of the operation rod 136*a* can be manually operated. A manual rod 138*a* as the operation member composed of the operation pin 134*a* and the operation rod 136*a* can be switched between a forward side connection position and a backward side release position with reference to a neutral position, and is held at the neutral position by the elastic member 114*a*. When the manual rod 138*a* is at the neutral position, the operation pin 134*a* is slidable in the play portion 11*a* without disturbing the back-and-forth movement of the sliding member 104*a*. When the manual rod 138*a* is disposed at the forward side connection position or the backward side release position, the sliding member 104*a* is disposed at the forward position or the backward position.

Next, the actuation of a selective actuation transmission mechanism of the power transmission apparatus 46*a*, 46*b* will be described.

When the first clutch mechanism 50*a* is switched by the electric drive mechanism 54*a*, the actuation is not transmitted from the sliding member 104*a* to the manual rod 138*a* owing the function of play formed between the sliding member 104*a* and the operation pin 134*a*. That is, the actuation is not transmitted from the electric drive mechanism 54*a* to the manual rod 138*a*.

The switching of the first clutch mechanism 50*a* by the manual drive mechanism 56*a* is explained.

In the case where the first clutch mechanism 50*a* is in the connection state and the sliding member 104*a* is at the forward position, the manual rod 138*a* is pulled and switched from the forward side connection position to the backward side release position. As a result, the sliding member 104*a* is switched from the forward position to the backward position, the first drive pin 52*a* is switched from the connection position to the release position, the first clutch mechanism 50*a* is switched from the connection position to the release position, and the first solenoid 100*a* is switched from the reset state to the attraction state. When the operation of the manual rod 138*a* is released, the manual rod 138*a* is reset to the neutral position.

In the case where the first clutch mechanism 50*a* is in the release state and the first sliding member 104*a* is at the backward position, the manual rod 138*a* is pushed in and switched from the backward side release position to the forward side connection position. As a result, the sliding member 104*a* is switched from the backward position to the forward position, the first drive pin 52*a* is switched from the release position to the connection position, the first clutch mechanism 50*a* is switched from the release position to the connection position, and the first solenoid 100*a* is switched from the attraction state to the reset state. When the operation of the manual rod 138*a* is released, the manual rod 138*a* is reset to the neutral position.

In any one of the switching operations, the actuation of the manual rod 138*a* is transmitted to the sliding member 104*a*, and the electric drive mechanism 54*a* is actuated. That is, the actuation is transmitted from the manual rod 138*a* to the electric drive mechanism 54*a*.

Therefore, the power transmission apparatus 46*a* in the present embodiment includes the following effect.

In the power transmission apparatus 46*a* in the present embodiment, even when the sliding member 104*a* is actuated by the electric drive mechanism 54*a*, the actuation is not transmitted from the sliding member 104*a* to the manual rod 138*a* owing to the play provided between the sliding member 104*a* and the manual rod 138*a* as long as the manual rod 138*a* is disposed at the neutral position.

While the clutch mechanism is switched between the connection state and the release state by the manual drive mechanism in the embodiments described above, the clutch mechanism may be switched by the manual drive mechanism only from the connection state to the release state or from the release state to the connection state. For example, the switching from the connection state to the release state may be only carried out by the manual drive mechanism, and the clutch mechanism may be switched by the electric drive mechanism at normal times, while the clutch mechanism may be switched to the release state by the manual drive mechanism in an emergency.

Other advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A power transmission apparatus for an electric bending endoscope comprising:

a power transmission mechanism to transmit power;

a clutch mechanism switchable between a connection state to permit the transmission of the power by the power transmission mechanism and a release state not to permit the transmission of the power by the power transmission mechanism;

an actuating member switchable between a connection position to bring the clutch mechanism into the connection state and a release position to bring the clutch mechanism into the release state, the actuating member being interlocked with the clutch mechanism;

an electric drive mechanism electrically switchable between a connection drive state to bring the actuating member into the connection position and a release drive state to bring the actuating member into the release position, the electric drive mechanism being interlocked with the actuating member; and a manual drive mechanism including an operation member manually switchable to at least one of a connection drive position to bring the actuating member into the connection position and a release drive position to bring the actuating member into the release position, and a selective actuation transmission mechanism provided between the operation member and the actuating member and to transmit the actuation of the operation member to the actuating member and absorb the actuation of the actuating member without transmitting the actuation to the operation member.

2. The power transmission apparatus for the electric bending endoscope according to claim 1, wherein the operation member is switchable from a neutral position to the at least one drive position, and the selective actuation transmission mechanism includes a selection member to be interlocked with the operation member and actuate the actuating member when the operation member is actuated from the neutral position, and a play portion provided between the actuating member and the selection member and to produce play between the actuating member and the selection member when the operation member is at the neutral position.

3. The power transmission apparatus for the electric bending endoscope according to claim 1, wherein the operation member is switchable from a neutral position to the at least one drive position, and the selective actuation transmission mechanism includes a selection member to be interlocked with the actuating member and to be actuated when the operation member is actuated from the neutral position, and a play portion provided between the selection member and the operation member and to produce play between the selection member and the operation member when the operation member is at the neutral position.

4. The power transmission apparatus for the electric bending endoscope according to claim 1, further comprising:

other power transmission mechanism to transmit power;

other clutch mechanism switched between a connection state to permit the transmission of the power by the other power transmission mechanism and a release state not to permit the transmission of the power by the other power transmission mechanism; and a coupling mechanism coupling the clutch mechanism to the other clutch mechanism so that the clutch mechanism and the other clutch mechanism are interlocked with each other.

5. The power transmission apparatus for the electric bending endoscope according to claim 4, further comprising:

other actuating member switchable between a connection position to bring the other clutch mechanism into the connection state and a release position to bring the other clutch mechanism into the release state, the other actuating member being interlocked with the other clutch mechanism; and other electric drive mechanism electrically switchable between a connection drive state to bring the other actuating member into the connection position and a release drive state to bring the other actuating member into the release position, the other electric drive mechanism being interlocked with the other actuating member.

6. The power transmission apparatus for the electric bending endoscope according to claim 1, wherein the electric drive mechanism is a self-holding type such that the drive state is held when electricity is not turned on.

7. The power transmission apparatus for the electric bending endoscope according to claim 1, further comprising: other power transmission mechanism to transmit power; other clutch mechanism switchable between a connection state to permit the transmission of the power by the other power transmission mechanism and a release state not to permit the transmission of the power by the other power transmission mechanism; other actuating member switchable between a connection position to bring the other clutch mechanism into the connection state and a release position to bring the other clutch mechanism into the release state, the other actuating member being interlocked with the other clutch mechanism; other electric drive mechanism electrically switchable between a connection drive state to bring the other actuating member into the connection position and a release drive state to bring the other actuating member into the release position, the other electric drive mechanism being interlocked with the other actuating member; other manual drive mechanism including other operation member manually switchable to at least one of a connection drive position to bring the other actuating member into the connection position and a release drive position to bring the other actuating member into the release position, and other selective actuation transmission mechanism provided between the other operation member and the other actuating member and to transmit the actuation of the other operation member to the other actuating member and absorb the actuation of the other actuating member without transmitting the actuation to the other operation member; and a central axis, wherein the power transmission mechanism, the actuating member, the clutch mechanism, the electric drive mechanism and the manual drive mechanism are arranged in rotational symmetry to the other power transmission mechanism, the other actuating member, the other clutch mechanism, the other electric drive mechanism and the other manual drive mechanism with respect to the central axis.

8. An electric bending endoscope comprising a power transmission apparatus, the power transmission apparatus including:

a power transmission mechanism to transmit power;

a clutch mechanism switchable between a connection state to permit the transmission of the power by the power transmission mechanism and a release state not to permit the transmission of the power by the power transmission mechanism;

an actuating member switchable between a connection position to bring the clutch mechanism into the connection state and a release position to bring the clutch mechanism into the release state, the actuating member being interlocked with the clutch mechanism;

an electric drive mechanism electrically switchable between a connection drive state to bring the actuating member into the connection position and a release drive state to bring the actuating member into the release position, the electric drive mechanism being interlocked with the actuating member; and a manual drive mechanism including an operation member manually switchable to at least one of a connection drive position to bring the actuating member into the connection position and a release drive position to bring the actuating member into the release position, and a selective actuation transmission mechanism provided between the operation member and the actuating member and to transmit the actuation of the operation member to the actuating member and absorb the actuation of the actuating member without transmitting the actuation to the operation member.

9. The electric bending endoscope according to claim 8, wherein the operation member is switchable from a neutral position to the at least one drive position, and the selective actuation transmission mechanism includes a selection member to be interlocked with the operation member and actuate the actuating member when the operation member is actuated from the neutral position, and a play portion provided between the actuating member and the selection member and to produce play between the actuating member and the selection member when the operation member is at the neutral position.

10. The electric bending endoscope according to claim 8, wherein the operation member is switchable from a neutral position to the at least one drive position, and the selective actuation transmission mechanism includes a selection member to be interlocked with the actuating member and to be actuated when the operation member is actuated from the neutral position, and a play portion provided between the selection member and the operation member and to produce play between the selection member and the operation member when the operation member is at the neutral position.

11. The power transmission apparatus for the electric bending endoscope according to claim 8, further comprising:

other power transmission mechanism to transmit power;

other clutch mechanism switched between a connection state to permit the transmission of the power by the other power transmission mechanism and a release state not to permit the transmission of the power by the other power transmission mechanism; and a coupling mechanism coupling the clutch mechanism to the other clutch mechanism so that the clutch mechanism and the other clutch mechanism are interlocked with each other.

12. The electric bending endoscope according to claim 11, further comprising:

other actuating member switchable between a connection position to bring the other clutch mechanism into the connection state and a release position to bring the other clutch mechanism into the release state, the other actuating member being interlocked with the other clutch mechanism; and other electric drive mechanism electrically switchable between a connection drive state to bring the other actuating member into the connection position and a release drive state to bring the other actuating member into the release position, the other electric drive mechanism being interlocked with the other actuating member.

13. The electric bending endoscope according to claim 8, wherein the electric drive mechanism is a self-holding type such that the drive state is held when electricity is not turned on.

14. The electric bending endoscope according to claim 8, further comprising: other power transmission mechanism to transmit power; other clutch mechanism switchable between a connection state to permit the transmission of the power by the other power transmission mechanism and a release state not to permit the transmission of the power by the other power transmission mechanism; other actuating member switchable between a connection position to bring the other clutch mechanism into the connection state and a release position to bring the other clutch mechanism into the release state, the other actuating member being interlocked with the other clutch mechanism; other electric drive mechanism electrically switchable between a connection drive state to bring the other actuating member into the connection position and a release drive state to bring the other actuating member into the release position, the other electric drive mechanism being interlocked with the other actuating member; other manual drive mechanism including other operation member manually switchable to at least one of a connection drive position to bring the other actuating member into the connection position and a release drive position to bring the other actuating member into the release position, and other selective actuation transmission mechanism provided between the other operation member and the other actuating member and to transmit the actuation of the other operation member to the other actuating member and absorb the actuation of the other actuating member without transmitting the actuation to the other operation member; and a central axis, wherein the power transmission mechanism, the actuating member, the clutch mechanism, the electric drive mechanism and the manual drive mechanism are arranged in rotational symmetry to the other power transmission mechanism, the other actuating member, the other clutch mechanism, the other electric drive mechanism and the other manual drive mechanism with respect to the central axis.

* * * * *